United States Patent
Stanton et al.

(10) Patent No.: US 9,796,977 B2
(45) Date of Patent: Oct. 24, 2017

(54) LOW MOLECULAR WEIGHT CYCLIC AMINE CONTAINING CATIONIC LIPIDS FOR OLIGONUCLEOTIDE DELIVERY

(71) Applicant: SIRNA THERAPEUTICS, INC., Cambridge, MA (US)

(72) Inventors: Matthew G. Stanton, Marlton, NJ (US); Gregory L. Beutner, Green Brook, NJ (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/719,513

(22) Filed: May 22, 2015

(65) Prior Publication Data

US 2015/0361434 A1    Dec. 17, 2015

Related U.S. Application Data

(63) Continuation of application No. 13/883,487, filed as application No. PCT/US2011/058498 on Oct. 31, 2011, now Pat. No. 9,067,882.

(60) Provisional application No. 61/410,472, filed on Nov. 5, 2010.

(51) Int. Cl.
| | |
|---|---|
| *A61K 9/51* | (2006.01) |
| *C07D 211/40* | (2006.01) |
| *C07D 223/08* | (2006.01) |
| *C12N 15/113* | (2010.01) |
| *C07D 207/12* | (2006.01) |

(52) U.S. Cl.
CPC ........ *C12N 15/1137* (2013.01); *A61K 9/5123* (2013.01); *C07D 207/12* (2013.01); *C07D 211/40* (2013.01); *C07D 223/08* (2013.01); *C12N 15/113* (2013.01); *C12N 2310/14* (2013.01); *C12N 2320/32* (2013.01)

(58) Field of Classification Search
CPC ... C07D 211/40; C07D 223/08; A61K 9/5123
See application file for complete search history.

(56) References Cited

U.S. PATENT DOCUMENTS

2010/0104629 A1    4/2010  Dande et al.

FOREIGN PATENT DOCUMENTS

WO    2010054384    5/2010

OTHER PUBLICATIONS

Cicchi et al. (CAPLUS Abstract of: Chemical Communications (2007), (14), 1424-1426).
Jauaraj et al. (CAPLUS Abstract of: Chemical Research in Toxicology (2003), 16(5), 637-643).
Akinc et al.,"Development of lipidoid-siRNA formulations for systemic delivery to the liver." Mol Ther. 17(5):872-879; 2009.
Bhattacharya et al., "Advances in gene delivery through molecular design of cationic lipids." Chem. Commun. 4632-4656; 2009.
Love et al., "Lipid-like materials for low-dose, in vivo gene silencing." Proc Natl Acad Sci USA; 107(5):1864-1869; 2010.
Majeti et al., "Enhanced Intravenous Transgene Expression in Mouse Lung Using Cyclic-Head Cationic Lipids." Chemistry & Biology, 11(4):427-437; 2004.
Nantz et al., "The benefit of hydrophobic domain asymmetry on the efficacy of transfection as measured by in vivo imaging." Mol Pharm. 7(3):786-794; Jun. 7, 2010.
Niculescu-Duvaz et al., "Structure-activity relationship in cationic lipid mediated gene transfection." Curr Med Chem. 10(14):1233-1261; 2003.
Zhi et al. Transfection Efficiency of Cationic Lipids with Different Hydrophobic Domains in Gene Delivery. Bioconjugate Chem., 21(4):563-577; 2010.

*Primary Examiner* — Robert Havlin
(74) *Attorney, Agent, or Firm* — Nixon Peabody LLP; David S. Resnick (57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids comprising at least one short lipid chain to enhance the efficiency and tolerability of in vivo delivery of siRNA.

5 Claims, 3 Drawing Sheets

LOW MOLECULAR WEIGHT CYCLIC AMINE CONTAINING CATIONIC LIPIDS FOR OLIGONUCLEOTIDE DELIVERY

CROSS REFERENCE TO RELATED APPLICATIONS

This application is a Continuation of U.S. patent application Ser. No. 13/883,487 filed May 3, 2013, which is 371 National Phase Entry of International Patent Application No. PCT/US2011/058498 filed on Oct. 31, 2011, which claims benefit under 35 U.S.C. 119(e) of the U.S. Provisional Application No. 61/410,472, filed Nov. 5, 2010, the contents of which are incorporated herein by reference in their entirety.

The Sequence Listing associated with this application is provided in text format in lieu of a paper copy, and is hereby incorporated by reference into the specification. The name of the text file containing the Sequence Listing is MRLMIS00047WOPCTSEQ. The text file is 3671 bytes, was created on Oct. 31, 2011, and is being submitted electronically via EFS-Web, concurrent with the filing of the specification.

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been previously disclosed. (See US patent applications: US 2006/0083780, US 2006/0240554, US 2008/0020058, US 2009/0263407 and US 200910285881 and PCT patent applications: WO 2009/086558, WO2009/127060, WO2009/132131, WO2010/042877, WO2010/054384, WO2010/054401, WO2010/054405, WO2010/054406 and WO2010/105209). See also Semple S. C. et al., Rational design of cationic lipids for siRNA delivery, *Nature Biotechnology*, 2010, 28, 172-176. Other cationic lipids are disclosed in US patent applications: US 2009/0263407, US 200910285881, US 2010/0055168, US 2010/0055169, US 2010/0063135, US 2010/0076055, US 2010/0099738 and US 2010/0104629.

Further, the specific cationic lipids cis and trans 1-methyl-3,4-bis-[((9Z,12Z)-octadeca-9,12-dienyl)oxy]-pyrrolidine are disclosed in WO2010/054384.

It is an object of the instant invention to provide a cationic lipid scaffold that demonstrates enhanced efficacy along with lower liver toxicity. The present invention employs low molecular weight cationic lipids comprising at least one short lipid chain to enhance the efficacy and tolerability of in vivo delivery of siRNA.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

DETAILED DESCRIPTION OF THE INVENTION

The various aspects and embodiments of the invention are directed to the utility of novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405, WO2010/054406 and WO2010/105209). See also Semple S. C. et al., Rational design of cationic lipids for siRNA delivery, Nature Biotechnology, published online 17 Jan. 2010; doi:10.1038/nbt.1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

A wherein:
$R^1$ is selected from H, $(C_1-C_6)$alkyl, heterocyclyl, polyether and polyamine, wherein said alkyl, heterocyclyl, polyether and polyamine are optionally substituted with one to three substituents selected from R';
n and m are independently selected from 0, 1, 2 and 3;
X is independently selected from a bond, O, NR", (C=O) O, O(C=O), (C=O)NR", NR"(C=O), O(C=O)O, NR"(C=O)NR", O(C=O)NR", and NR"(C=O)O;
$L_1$ is selected from $C_4-C_{24}$ alkyl and $C_4-C_{24}$ alkenyl, said alkyl and alkenyl are optionally substituted with one or more substituents selected from R'; and
$L_2$ is selected from $C_3-C_9$ alkyl and $C_3-C_9$ alkenyl, said alkyl and alkenyl are optionally substituted with one or more substituents selected from R';
R' is independently selected from halogen, R", OR", SR", CN, $CO_2R"$ and $CON(R")_2$;
R" is independently selected from H and $(C_1-C_6)$alkyl;
or any pharmaceutically acceptable salt or stereoisomer thereof.

In a second embodiment, the invention features a compound having Formula A, wherein:
$R^1$ is H or methyl;
n and m are 1;
X is O;
$L_1$ is selected from $C_{12}$-$C_{24}$ alkyl and $C_{12}$-$C_{24}$ alkenyl; and
$L_2$ is selected from $C_3$-$C_9$ alkyl and $C_3$-$C_9$ alkenyl;
or any pharmaceutically acceptable salt or stereoisomer thereof.

Specific cationic lipids are:
trans-1-Methyl-3-[((9Z,12Z)-octadeca-9,12-dienyl)oxy]-4-octyloxy-pyrrolidine (Compound 4);
trans-1-methyl-3-[(9Z)-octadec-9-en-1-yloxy]-4-(octyloxy)pyrrolidine (Compound 5);
tram-1-methyl-3-[(12Z)-octadec-12-en-1-yloxy]-4-(octyloxy)pyrrolidine (Compound 6);
trans-3-[(3,7-dimethyloctyl)oxy]-1-methyl-4-[(9Z,12Z)-octadeca-9,12-dien-1-yloxy]pyrrolidine (Compound 7); and
cis-1-methyl-3-[(9Z,12Z)-octadeca-9,12-dien-1-yloxy]-4-(octyloxy)pyrrolidine (Compound 11)
or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended, to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl" are:

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyether" means compounds having two or more ether groups. Examples include poly(ethylene) glycols.

As used herein, "polyamine" means compounds having two or more amino groups. Examples include putrescine, cadaverine, spermidine, and spermine.

As used herein, "halogen" means Br, Cl, F and I.

In an embodiment of Formula A, $R^1$ is selected from H and $(C_1-C_6)$alkyl, wherein said alkyl is optionally substituted with one to three substituents selected from R'.

In an embodiment of Formula A, $R^1$ is selected from H, methyl, ethyl and propyl, wherein said methyl, ethyl and propyl are optionally substituted with one to three substituents selected from R'.

In an embodiment of Formula A, $R^1$ is selected from H, methyl, ethyl and propyl.

In an embodiment of Formula A, $R^1$ is methyl.

In an embodiment of Formula A, R' is selected from H, methyl, ethyl and propyl, wherein said methyl, ethyl and propyl are optionally substituted with one or more halogen and OH.

In an embodiment of Formula A, n is 0, 1, 2 or 3.
In an embodiment of Formula A, n is 1 or 2.
In an embodiment of Formula A, n is 1.
In an embodiment of Formula A, m is 0, 1, 2 or 3.
In an embodiment of Formula A, m is 1 or 2.
In an embodiment of Formula A, m is 1.
In an embodiment of Formula A, X is a bond, O, NR", (C=O)O, NR"(C=O), O(C=O)O, NR"(C=O)NR", O(C=O)NR", or NR"(C=O)O.
In an embodiment of Formula A, X is (C=O)O or O.
In an embodiment of Formula A, X is O.
In an embodiment of Formula A, $L_1$ is selected from $C_4-C_{24}$ alkyl and $C_4-C_{24}$ alkenyl, which are optionally substituted with halogen and OH.
In an embodiment of Formula A, $L_1$ is selected from $C_4-C_{24}$ alkyl and $C_4-C_{24}$ alkenyl.
In an embodiment of Formula A, $L_1$ is selected from $C_{12}-C_{24}$ alkyl and $C_{12}-C_{24}$ alkenyl, which are optionally substituted with halogen and OH.
In an embodiment of Formula A, $L_1$ is selected from $C_{12}-C_{24}$ alkyl and $C_{12}-C_{24}$ alkenyl.
In an embodiment of Formula A, $L_1$ is selected from $C_4-C_{24}$ alkenyl.
In an embodiment of Formula A, $L_1$ is selected from $C_{12}-C_{24}$ alkenyl.
In an embodiment of Formula A, $L_1$ is $C_{18}$ alkenyl.
In an embodiment of Formula A, $L_1$ is:

In an embodiment of Formula A, $L_2$ is selected from $C_3-C_9$ alkyl and $C_3-C_9$ alkenyl, which are optionally substituted with halogen and OH.
In an embodiment of Formula A, $L_2$ is selected from $C_5-C_9$ alkyl and $C_5-C_9$ alkenyl, which are optionally substituted with halogen and OH.
In an embodiment of Formula A, $L_2$ is selected from $C_7-C_9$ alkyl and $C_7-C_9$ alkenyl, which are optionally substituted with halogen and OH.
In an embodiment of Formula A, $L_2$ is selected from $C_3-C_9$ alkyl and $C_3-C_9$ alkenyl.

In an embodiment of Formula A, $L_2$ is selected from $C_5-C_9$ alkyl and $C_5-C_9$ alkenyl.
In an embodiment of Formula A, $L_2$ is selected from $C_7-C_9$ alkyl and $C_7-C_9$ alkenyl.
In an embodiment of Formula A, $L_2$ is $C_3-C_9$ alkyl.
In an embodiment of Formula A, $L_2$ is $C_5-C_9$ alkyl.
In an embodiment of Formula A, $L_2$ is $C_7-C_9$ alkyl.
In an embodiment of Formula A, $L_2$ is $C_8$ alkyl.
In an embodiment of Formula A, "heterocyclyl" is pyrolidine, piperidine, morpholine, imidazole or piperazine.
In an embodiment of Formula A, "polyamine" is putrescine, cadaverine, spermidine or spermine.
In an embodiment of Formula A, "polyether" is poly(ethylene) glycol(s).
In an embodiment, "alkyl" is a straight chain saturated aliphatic hydrocarbon having the specified number of carbon atoms.
In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing cationic lipids are either commercially available or are readily prepared by one of ordinary skill in the art.

Synthesis of cyclic amine containing cationic lipids is a linear process starting from cyclic dihydroxy amines i. Stepwise etherification to give it followed by cleavage of the benzyl group to give iii and reductive amination gives products of the type iv.

Example 1

1-Methyl-3-[((9Z 12Z)-octadeca-9,12-dienyl)oxy]-4-octyloxy-pyrrolidine (4)

1-Benzyl-3,4-dihydroxy pyrrolidine sulfonic aid salt (1)

In a 3N 5 L RBF with overhead stirrer and reflux condenser, the DL-1,4-dibromo butane diol (100 g, 403 mmol), benzyl amine (39.7 ml, 363 mmol), potassium iodide (3.35 g, 20.17 mmol) and diisopropylethylamine (DIPEA, 70.3 ml, 403 mmol) were suspended in 500 mL dioxane and heated to 110° C. overnight. After 17 h cooled at 80° C., added 750 mL 1M aqueous K₂CO₃ and 750 mL ethyl acetate (EtOAc). Allowed to cool to 23° C. and separated layers. Extracted with 500 mL EtOAc and then dried combined organics over Na₂SO₄. Filtered and concentrated to 400 mL solution. Added benzene sulfonic acid (38.3 g, 242 mmol) in 200 mL EtOAc slowly over 1 h. After 16 h at 23° C., cooled to 0° C. and filtered. Washed cake with 200 mL methyl tert-butyl ether (MTBE) and then dried under vacuum at 40° C. for 6 h to give 73.8 g of 1 as an off-white solid (52% yield). $^1$H NMR (400 MHz, CD$_3$OD) δ 7.85 (m, 2H), 7.65-7.41 (m, 8H), 4.42 (m, 211), 4.28 (m, 2H), 3.79 (dd, J=12.7, 4.2 Hz, 1H), 3.51 (dd, J=12.2, 3.4 Hz, 1H), 3.38 (d, J=12.2 Hz, 11), 3.25 (d, J=12.7 Hz, 1H).

1-Benzyl-3[((9Z,12Z)-octadeca-9,12-dienyl)oxy]-4-octyloxy-pyrrolidine (2)

In 500 mL 3N RBF, compound 1 (18 g, 51.2 mmol) and triethylamine (0.714 ml, 5.12 mmol) were suspended in 180 mL toluene for addition of the sodium hydride (4.30 g, 108 mmol). Heated suspension to 50° C. for 1 h. Cooled back to 23° C. and then added the n-octyl mesylate (10.67 g, 51.2 mmol). Heated slurry up to 80° C. for 18 h. Cooled to 23° C. and poured into 200 mL 1M K$_2$CO$_3$. Extracted with methyl tert-butyl ether (MTBE) and then dried combined layers over Na$_2$SO$_4$. Filtered, concentrated and purified oil by silica gel chromatography to obtain 7.22 g of a slightly yellow oil. In 500 mL 3N RBF, 4.04 g of the aforementioned oil (13.23 mmol) and triethylamine (0.184 ml, 1.323 mmol) was dissolved in 80 mL toluene for addition of the sodium hydride (0.582 g, 14.55 mmol). Heated suspension to 50° C. for 1 h. Cooled back to 23° C. and then added the linoleoyl mesylate (5.01 g, 14.55 mmol). Heated slurry up to 80° C. for 21 h or until complete disappearance of the starting material was observed by HPLC. Cooled to 23° C., diluted with 100 mL hexane and washed with 100 mL 1M K$_2$CO$_3$. Extracted aqueous layer with 0.100 mL hexane and then washed combined organic layers with 100 mL brine and dried over MgSO$_4$. Filtered and concentrated. Purified by silica gel chromatography to obtain 5.02 g of 2 as a clear oil (33% yield over 2 steps). $^1$H NMR (400 MHz, CDCl$_3$) δ 7.28 (m, 5H), 5.40 (m, 48), 3.85 (Ψt, J 4.8 Hz, 2H), 3.61 (m, 2H), 3.42 (m, 4H), 2.88 (dd, J=9.7, 6.1 Hz, 2H), 2.79 (Ψt, J=6.4 Hz, 2H), 2.51 (dd, J=10.1, 4.2 Hz, 2), 2.06 (q. J=6.7 Hz, 211), 1.56 (q, 4H), 1.41-1.29 (m, 26H), 0.9 (m, 68).

3-[((9Z,12Z)-octadeca-9,12-dienyl)oxy]-4-octyloxy-pyrrolidin (3)

In a 500 mL 3N RBF, compound 2 (6.32 g, 11.41 mmol) was dissolved in 60 mL dichloromethane (DCM) at 0° C. for addition of the DIPEA (5.96 ml, 34.2 mmol) and chloroethyl chloroformate (3.73 ml, 34.2 mmol). Aged at for 3 h at 23° C. or until complete disappearance of 2 is observed by HPLC. Concentrated down and then added 60 mL methanol (MeOH). Continued aging at 23° C. After an additional 18 h, concentrated to a thick oil and then partitioned between 200 mL hexane and 200 mL 1M K$_3$CO$_3$. Extracted with hexane and then dried over Na$_2$SO$_4$. Filtered and concentrated before purification by silica gel chromatography to obtain 2.70 g of 3 as a yellow oil (51% yield). $^1$H NMR (400 MHz, CDCl$_3$) δ 5.38 (m, 4H), 3.78 (m, 2H), 3.45 (m, 4H), 3.11 (dd, J=12.4, 5.2 Hz, 2H), 2.84 (dd, J=12.5, 2.6 Hz, 2H), 2.79 (Pt, J=6.6 Hz, 2H), 2.07 (q, J=6.7 Hz, 4H), 1.55 (q, J=6.6 Hz, 4H), 1.41-1.16 (m, 26H), 0.90 (m, 6H).

1-Methyl-3-[((9Z,12Z)-octadeca-9,12-dienyl)oxy]-4-octyloxy-pyrrolidine (4)

In a 500 mL RBF, compound 3 (4.24 g, 9.14 mmol) was dissolved in 80 mL tetrahydrofuran (THF) for addition of 20 mL glacial acetic acid. To this was added the paraformaldehyde (2.75 g, 91 mmol) followed by the pyridine-borane complex (1.829 ml, 18.28 mmol). Aged at 23° C. for 20 h or until complete disappearance of 3 was observed by HPLC. Added 100 mL hexane and 100 mL 1M K$_2$CO$_3$ and stirred until bubbling had subsided. Separated layers, extracted with 100 mL hexane and washed combined organics with 100 mL brine. Dried over Na$_2$SO$_4$, filtered and concentrated before purification by silica gel chromatography to obtain 1.75 g of 4 as a clear oil (41% yield). $^1$H NMR (400 MHz, CDCl$_3$) δ 5.37 (m, 4H), 3.85 (Ψt, J=4.4 Hz, 2H), 3.44 (m, 4H), 2.93 (dd, J=10.2, 6.2 Hz, 2H), 2.79 (Ψt, J=6.5 Hz, 2H), 2.6 (m, 2H), 2.39 (s, 3H), 2.06 (q, J=7.6 Hz, 4H), 1.58 (m, 4H), 1.41-1.31 (m, 26H), 0.90 (m, 6H).

Compounds 5-7 were prepared in a manner analogous to that described for Compound 4.

1-methyl-3-[(9-octadec-9-en-1-yloxy]-4-(octyloxy)pyrrolidine (5)

LCI/MS (M+H)=480.6.

1-methyl-3-[(12Z)-octadec-12-en-1-yloxy]-4-(octyloxy)pyrrolidine (6)

$^1$H NMR (400 MHz, CDCl$_3$) δ 5.37 (m, 2K), 3.85 (Ψt, J=4.4 Hz, 2H), 3.48 (m, 4H), 2.85 (dd, J=10.2, 6.2 Hz, 2H), 2.48 (m, 2H), 2.34 (s, 3H), 2.06 (m, 4H), 1.58 (m, 4H), 1.41-1.31 (m, 30H), 0.90 (m, 6H).

3-[(3,7-dimethyloctyl)oxy]-1-methyl-4-[(9Z,12Z)-octadeca-9,12-dien-1-yloxy]pyrrolidine (7)

LC/MS (M+H) 506.6.

Example 2

Cis-1-methyl-3-[(9Z,12Z)-octadeca-9,12-dien-1-yloxy]-4-(octyloxy)pyrrolidine (11)

Benzyl 3,4-dihydroxypyrrolidine-1-carboxylate (9)

In a 500 mL RBF, the Cbz Pyrroline (15 g, 73.8 mmol) was dissolved in a mixture of 100 mL THP, 60 mL t-BuOH and 40 mL water for addition of the NMO (30.6 ml, 148 mmol) solution followed by the osmium tetraoxide (0.925 ml, 0.074 mmol) solution. Heated in a 70 C oil bath. Solution slowly went from yellow to brown. After 2 h, cooled to RT and added 50 mL 10% aqueous NaHSO3. Concentrated and partitioned between 100 mL brine and 100 mL EtOAc. Separated layers and extracted with 100 mL EtOAc. Dried over MgSO4, filtered and concentrated to 22.3 g of thick yellow oil. Flash column chromatography from 50-100% EtOAc in hexane provided compound 9. $^1$H NMR (400 MHz, CDCl$_3$) δ 7.35 (m, 5H), 5.22 (s, 2H), 4.42 (m, 4H), 3.63 (m, 2H), 3.42 (m, 3H), 3.20 (min, 1H).

Benzyl 3-[(9Z,12Z)-octadeca-9,12-dien-1-yloxy]-4-(octyloxy)pyrrolidine-1-carboxylate (10)

In 2500 mL RBF, compound 9 (9.7 g, 40.0 mmol) and triethylamine (0.558 ml 4.0 mmol) were suspended in 100 mL toluene for addition of the sodium hydride (1.76 g, 44 mmol). Heated suspension to 50° C. for 1 h. Cooled back to 23° C. and then added the linoleyl mesylate (13.8 g, 40.0 mmol). Heated slurry up to 80° C. for 18 h. Cooled to 23° C. and poured into 200 mL 1M K$_2$CO$_3$. Extracted with methyl tert-butyl ether (MT'BE) and then dried combined layers over Na$_2$SO$_4$, Filtered, concentrated and purified oil by silica gel chromatography to obtain monoalkylated product as a slightly yellow oil. In 250 mL RBF, 8 g of the aforementioned oil (16.47 mmol) and triethylamine (0.23 ml, 1.65 mmol) was dissolved in 100 mL toluene for addition of the sodium hydride (0.0.725 g, 18.12 mmol). Heated suspension to 50° C. for 1 h. Cooled back to 23° C. and then added the n-octyl mesylate (3.77 g, 18.12 mmol). Heated slurry up to 80° C. for 21 h or until complete disappearance of the starting material was observed by HPLC. Cooled to 23° C., diluted with 100 mL hexane and washed with 100 mL 1M K$_2$CO$_3$. Extracted aqueous layer with 100 mL hexane and then washed combined organic layers with 100 mL brine and dried over MgSO$_4$. Filtered and concentrated. Purified by silica gel chromatography to obtain 8.4 g of 10 as a clear oil. Product contains some octyl mesylate but was carried into next reaction.

Cis-1-methyl-3-[(9Z,12Z)-octadeca-9,12-dien-1-yloxy]-4-(octyloxy)pyrrolidine (11)

In a 100 mL RBF fitted with reflux condenser, compound 10 (4 g, 6.69 mmol) was dissolved in 26 mL THF for addition of the lithium aluminum hydride (13.38 ml, 13.38 mmol). Heated to reflux in a 85 C oil bath. After 2 h, HPLC shows complete disappearance of the SM. Cooled to RT and poured into 200 mL 1M K2CO3 and 200 mL MTBE. Stirred for 30 min, separated layers and then extracted with 100 mL MTBE. Dried combined organics over Na2SO4, filtered through Celite and concentrated. Flash chromatography (10-30% IPA in DCM) provided compound 11 as a clear oil. $^1$H NMR (400 MHz, CDCl$_3$) δ 5.39 (m, 4H), 3.93 (m, 2H), 3.50 (m, 4H), 3.04 (m, 2H), 2.79 (m, 2H), 2.48 (m, 2H), 2.39 (s, 3H), 2.08 (n, 4H), 1.62 (m, 4H), 1.40-1.25 (m, 26H), 0.91 (m, 6H).

Compound 12 is DLinKC2DMA as described in *Nature Biotechnology*, 2010, 28, 172-176, WO 2010/042877 A1, WO 2010/048536 A2, WO 2010/088537 A2, and WO 2009/127060 A1.

(12)

Compound 13 is MC3 as described in WO 2010/054401, and WO 2010/144740 A1.

(13)

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC40/48/2/10;
Cationic Lipid/Cholesterol/PEG-DMG/DSPC40/48/2/10; and
Cationic Lipid/Cholesterol/PEG-DMG/DSPC58/30/2/10.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole percent range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10 –600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM NaClO$_4$, 10 mM Tris, 20% EtOH, pH 7.0 and B: 250 mM NaClO$_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

$$\text{Encapsulation rate} = (1 - \text{free siRNA/total siRNA}) \times 100\%$$

3) Particle Size and Polydispersity

RDVs containing 1 µg siRNA are diluted to a final volume of 3 ml with 1×PBS. The Particle Size and Polydispersity of the Samples is Measured by a Dynamic Light Scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 g siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 µm particle size) column with CAD at 60° C. The mobile phase is composed of A: 0.1% TFA in $H_2O$ and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min: and 5% mobile phase A and 95% mobile phase B from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios were identified:

Nominal Composition;
Cationic Lipid/Cholesterol/PEG-DMG 60/38/2; and
Cationic Lipid/Cholesterol/PEG-DMG/DSPC 58/30/2/10.

Oligonucleotide synthesis is well known in the art. (See US patent applications: US 2006/0083780, US 200610240554, US 2008/0020058, US 2009/0263407 and US 2009/0285881 and PCT patent applications: WO 2009/086558. WO2009/127060, WO2009/132131, WO2010/042877, WO2010/054384, WO2010/054401, WO2010/054405 and WO2010/054406). The Luc siRNA incorporated in the LNPs disclosed and utilized in the Examples were synthesized via standard solid phase procedures.

Luc siRNA (SEQ. ID. NO.: 1)
5'-iB-A*U*AAGGC*U*A*U*GAAGAGA*U*ATT-iB 3'

(SEQ. ID. NO.: 2)
3'-UU*U*A*U*UCCGA*U*A*C*U*UCUC*U*AU-5'
AUGC-Ribose
iB-Inverted deoxy abasic
UC-2' Flouro
AGT-2' Deoxy
AGU-2' OCH₃

Nominal Composition

Cationic Lipid/Cholesterol/PEG-DMG 60/38/2

Cationic Lipid/Cholesterol/PEG-DMG/DSPC 40/48/2/10

Cationic Lipid/Cholesterol/PEG-DMG/DSPC 58/30/2/10

ApoB siRNA (SEQ ID NO.: 3)
5'-iB-CUUUAACAAUUCCUGAAAUTsT-iB-3'

(SEQ ID NO.: 4)
3'-UsUGAAAUUGUUAAGGACUsUsUsA-5'
AUGC-Ribose
iB-Inverted deoxy abasic
UC-2' Flouro
AGT-2' Deoxy
AGU-2' OCH₃
UsA-phophorothioate linkage Example 1

Mouse In Vivo Evaluation of Efficacy

LNPs utilizing Compound 4, in the nominal compositions described immediately above, were evaluated for in vivo efficacy. The siRNA targets the mRNA transcript for the firefly (*Photinus pyralis*) luciferase gene (Accession #M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 µL. After a four minute incubation period mice are anesthetized with isoflurane and placed in the IVIS imager. The RDVs (containing siRNA) in PBS vehicle were tail vein injected in a volume of 0.2 mL. Final dose levels ranged from 0.1 to 0.5 mg/kg siRNA. PBS vehicle alone was dosed as a control. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Systemic administration of the luciferase siRNA. RDVs decreased luciferase expression in a dose dependant manner. Greater efficacy was observed in mice dosed with Compound 4 containing RDVs than with the RDV containing the trans 1-methyl-3,4-bis-[((9Z,12Z)-octadeca-9,12-dienyl)oxy]-pyrrolidine (Compound A) as disclosed in WO2010/054384.

Example 2

Rat In Vivo Evaluation of Efficacy and Toxicity

Figure 1:
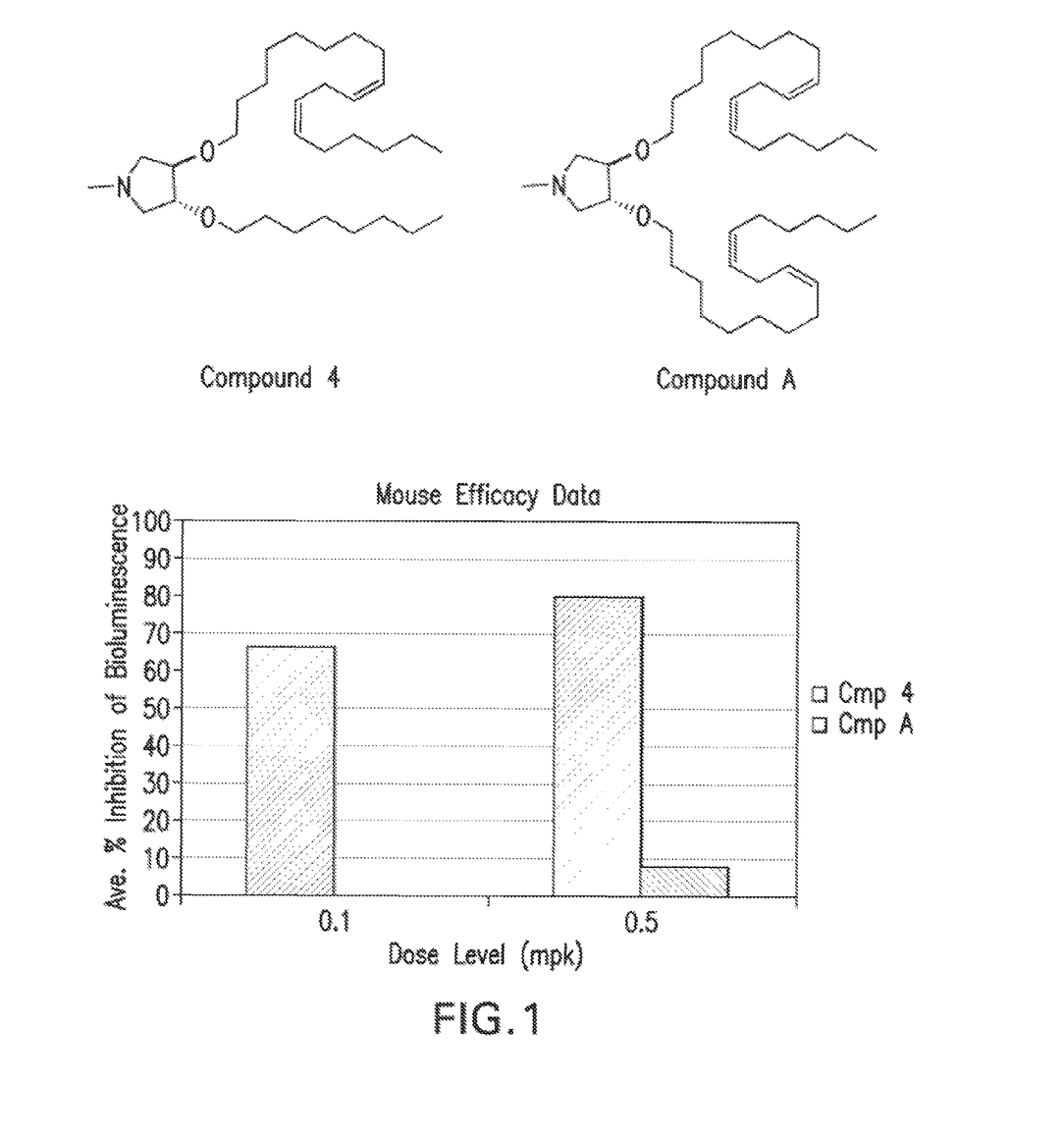
FIG. 1: Comparison of LNP (Compound 4) efficacy in mice.
Figure 2:
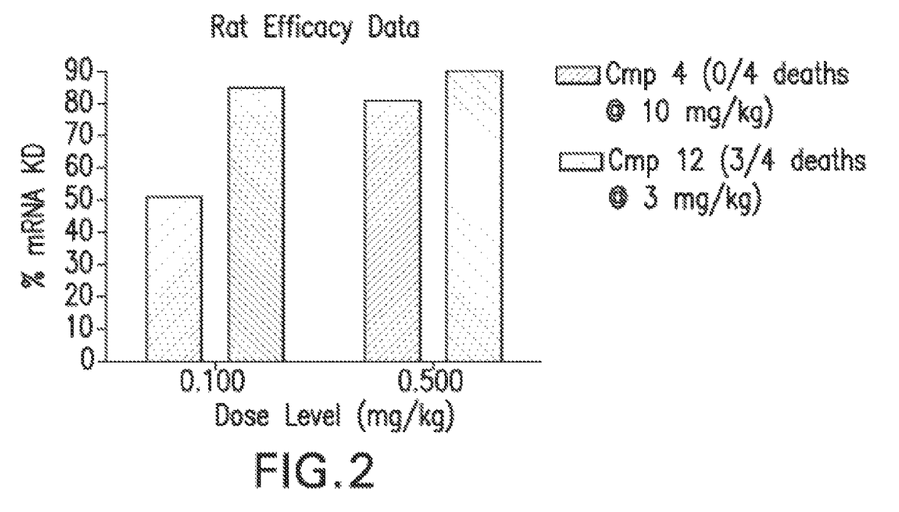
FIG. 2: LNP (Compound 4) efficacy and tolerability in rats.

LNPs utilizing compounds in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession #NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 gauge butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat #RN01499054_m1). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Biosystems Cat. No. Mm00478295_m1). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat#03039631) and aspartate aminotransferase (Cat#03039631) reagents. Modestly decreased efficacy but significantly improved tolerability was observed in rats dosed with Compound 4 containing RDV than with the RDV containing the cationic lipid DLinKC2DMA (Compound 12, FIG. 2).

Example 3

Determination of Cationic Lipid Levels in Rat Liver

Liver tissue was weighed into 20-ml vials and homogenized in 9 v/w of water using a (GenoGrinder 2000 (OPS Diagnostics, 1600 strokes/min, 5 min). A 50 µL aliquot of each tissue homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was then transferred to separate wells of a 96-well plate and 10 µl samples were directly analyzed by LCMS-MS.

Standards were prepared by spiking known amounts of a methanol stock solution of compound into untreated rat liver homogenate (9 vol water/weight liver). Aliquots (50 µL) each standard/liver homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was transferred to separate wells of a 96-well plate and 10 µl of each standard was directly analyzed by LC/MS-MS.

Absolute quantification versus standards prepared and extracted from liver homogenate was performed using an Aria LX-2 HPLC system (Thermo Scientific) coupled to an API 4000 triple quadrupole mass spectrometer (Applied Biosystems). For each run, a total of 10 µL sample was injected onto a BDS Hypersil C8 HPLC column (Thermo, 50×2 mm, 3 µm) at ambient temperature.

Mobile Phase A: 95% H2O/5% methanol/10 mM ammonium formate/0.1% formic acid Mobile Phase B: 40% methanol/60% n-propanol/10 mM ammonium formate/0.1% formic acid The flow rate was 0.5 mL/min and gradient elution profile was as follows: hold at 80% A for 0.25 min, linear ramp to 100% B over 1.6 min, hold at 100% B for 2.5 min, then return and hold at 80% A for 1.75 min. Total run time was 5.8 min. API 4000 source parameters were CAD: 4, CUR: 15, GS1: 65, GS2: 35, IS: 4000, TEM: 550. CXP: 15, DP: 60, EP: 10.

Figure 3:
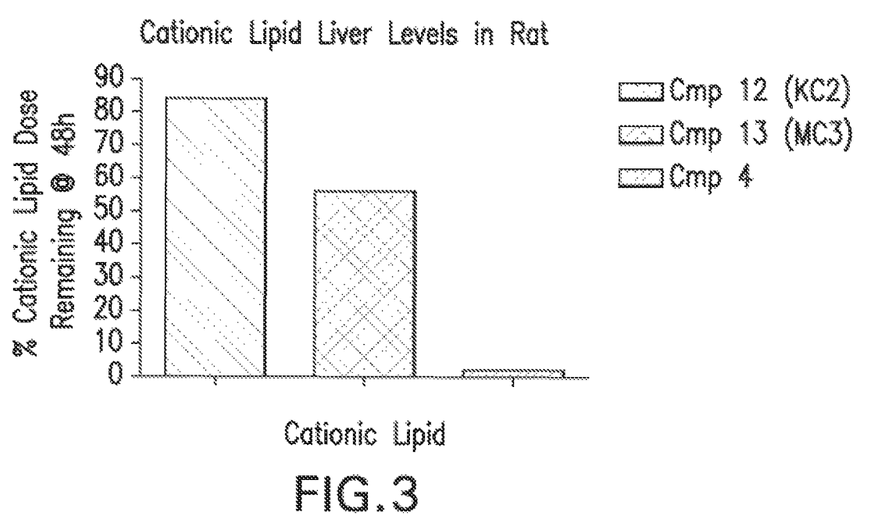
FIG. 3: Cationic lipid (Compound 4) levels in rat liver.

In rats dosed with Compound 4 (0.5 mg/kg) containing RDV, liver levels were much lower than the RDV containing the cationic lipid DLinKC2DMA (Compound 12, also 0.5 mg/kg) or MC3 (Compound 13, also 0.5 mg/kg. FIG. 3).

What is claimed is:

1. A cationic lipid of Formula A:

wherein:

$R^1$ is selected from H and $(C_1-C_6)$alkyl, wherein said alkyl is optionally substituted with one to three substituents selected from R";

n is 1 and m is 2 or 3; or m is 1 and n is 2 or 3;

X is O;

$L_1$ is $C_{12}-C_{24}$ alkenyl, said alkenyl optionally substituted with one or more substituents selected from R"; and $L_2$ is unsubstituted $C_3-C_9$ alkyl;

R" is independently selected from H and $(C_1-C_6)$alkyl;

or any pharmaceutically acceptable salt or stereoisomer thereof.

2. A lipid nanoparticle comprising a cationic lipid according to claim 1.

3. The lipid nanoparticle according to claim 2 further comprises an oligonucleotide.

4. The lipid nanoparticle according to claim 3 wherein the oligonucleotide is siRNA or miRNA.

5. The lipid nanoparticle according to claim 4 wherein the oligonucleotide is siRNA.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(1)
<223> OTHER INFORMATION: 2'-deoxy
<221> NAME/KEY: misc_feature
<222> LOCATION: (2)...(2)
<223> OTHER INFORMATION: 2'-fluoro
<221> NAME/KEY: misc_feature
<222> LOCATION: (3)...(6)
<223> OTHER INFORMATION: 2'-deoxy
<221> NAME/KEY: misc_feature
```

```
<222> LOCATION: (7)...(8)
<223> OTHER INFORMATION: 2'-fluoro
<221> NAME/KEY: misc_feature
<222> LOCATION: (9)...(9)
<223> OTHER INFORMATION: 2'-deoxy
<221> NAME/KEY: misc_feature
<222> LOCATION: (10)...(10)
<223> OTHER INFORMATION: 2'-fluoro
<221> NAME/KEY: misc_feature
<222> LOCATION: (11)...(17)
<223> OTHER INFORMATION: 2'-deoxy
<221> NAME/KEY: misc_feature
<222> LOCATION: (18)...(18)
<223> OTHER INFORMATION: 2'-fluoro
<221> NAME/KEY: misc_feature
<222> LOCATION: (19)...(21)
<223> OTHER INFORMATION: 2'-deoxy

<400> SEQUENCE: 1
auaaggcuau gaagagauat t                                          21

<210> SEQ ID NO 2
<211> LENGTH: 21
<212> TYPE: RNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(3)
<223> OTHER INFORMATION: ribose
<221> NAME/KEY: misc_feature
<222> LOCATION: (4)...(9)
<223> OTHER INFORMATION: 2'-fluoro
<221> NAME/KEY: misc_feature
<222> LOCATION: (10)...(10)
<223> OTHER INFORMATION: 2'-o-methyl
<221> NAME/KEY: misc_feature
<222> LOCATION: (11)...(11)
<223> OTHER INFORMATION: 2'-fluoro
<221> NAME/KEY: misc_feature
<222> LOCATION: (12)...(13)
<223> OTHER INFORMATION: 2'-o-methyl
<221> NAME/KEY: misc_feature
<222> LOCATION: (14)...(17)
<223> OTHER INFORMATION: 2'-fluoro
<221> NAME/KEY: misc_feature
<222> LOCATION: (18)...(18)
<223> OTHER INFORMATION: 2'-o-methyl
<221> NAME/KEY: misc_feature
<222> LOCATION: (19)...(19)
<223> OTHER INFORMATION: 2'-fluoro
<221> NAME/KEY: misc_feature
<222> LOCATION: (20)...(21)
<223> OTHER INFORMATION: 2'-o-methyl

<400> SEQUENCE: 2
uuuauuccga uacuucucua u                                          21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (5)..(6)
```

```
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 3
cuuuaacaau uccugaaaut t                                          21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (1)..(4)
<223> OTHER INFORMATION: phophorothioate linkage
<220> FEATURE:
<221> NAME/KEY: misc_feature
<222> LOCATION: (4)..(5)
<223> OTHER INFORMATION: 2' O-methyl
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
```

```
<222> LOCATION: (20)..(21)
<223> OTHER INFORMATION: phophorothioate linkage
<220> FEATURE:
<221> NAME/KEY: misc_feature
<222> LOCATION: (20)..(21)
<223> OTHER INFORMATION: 2' O-methyl

<400> SEQUENCE: 4
auuucaggaa uuguuaaagu u                                            21
```